United States Patent [19]
Fornarelli

[11] Patent Number: 5,205,811
[45] Date of Patent: Apr. 27, 1993

[54] BABY BLANKET WITH HEARTBEAT SIMULATOR

[76] Inventor: Belinda J. Fornarelli, 1636 N. 21st Ave., Melrose Park, Ill. 60160

[21] Appl. No.: 816,230

[22] Filed: Jan. 3, 1992

[51] Int. Cl.⁵ ............................................. A61M 21/00
[52] U.S. Cl. ............................................. 600/28
[58] Field of Search ............................. 600/26-28

[56] References Cited

U.S. PATENT DOCUMENTS

| | | | |
|---|---|---|---|
| 3,292,611 | 12/1966 | Belkin | 600/28 |
| 3,419,923 | 1/1969 | Cowan | 600/27 |
| 3,994,282 | 11/1976 | Moulet | 600/28 |
| 4,124,022 | 11/1978 | Gross | 600/28 |
| 4,941,453 | 7/1990 | Shakas et al. | 600/28 |
| 5,063,912 | 11/1991 | Hughes | 600/28 |

FOREIGN PATENT DOCUMENTS 9113647  9/1991  World Int. Prop. O. ............ 600/28

Primary Examiner—Lee S. Cohen
Assistant Examiner—J. P. Lacyk
Attorney, Agent, or Firm—Charles F. Meroni, Jr.

[57] ABSTRACT

The infant blanket is of the comforter type and includes therein a foam form having a cavity therein within which a heartbeat simulator rests. The simulator is preferably pressure activated and access to same is provided by means of a zipper strategically placed in one surface of the blanket.

12 Claims, 2 Drawing Sheets

BABY BLANKET WITH HEARTBEAT SIMULATOR

BACKGROUND OF THE INVENTION

The present invention relates to a baby blanket incorporating a heartbeat simulator therein, the simulator being activated by placement of an infant's torso thereupon.

PRIOR ART

Heretofore, heartbeat simulators have been proposed for use in dolls as disclosed in U.S. Pat. Nos. 3,563,229; 4,166,337; and 4,605,380.

Also, therapeutic use of a heartbeat simulator in an infant bed is disclosed in U.S. Pat. Nos. 4,934,997 and 4,947,832.

However, it has not heretofore been proposed to provide a comforter type infant blanket which incorporates a simulator therein for soothing an infant to sleep.

SUMMARY OF THE INVENTION

According to the invention there is provided an infant blanket which is the form of a thick comforter and includes therein a heartbeat simulator encased within a foam form having a thickness substantially equal to that of the reminder of the blanket.

Yet other features of my invention relate to an infant blanket in the form of a comforter in combination with a removable heartbeat simulator, the simulator being encased within a foam form and placed within the blanket, the simulator being pressure activated by placement of the weight of an infant's torso in a manner to overlie the simulator.

Still other and further features of my invention relate to an infant blanket of a thick comforter type comprising a shell having batting therein, the batting having a pouch formed therein, a foam form defining a cavity therein and being sized and configured to seat within said pouch, and a heartbeat simulator, the cavity in the foam form conforming to the shape of the simulator and receiving same therein, said pouch being substantially centered within the blanket and the blanket shell including a zipper therein overlying the pouch.

DESCRIPTION OF THE PREFERRED EMBODIMENT

Figure 1:
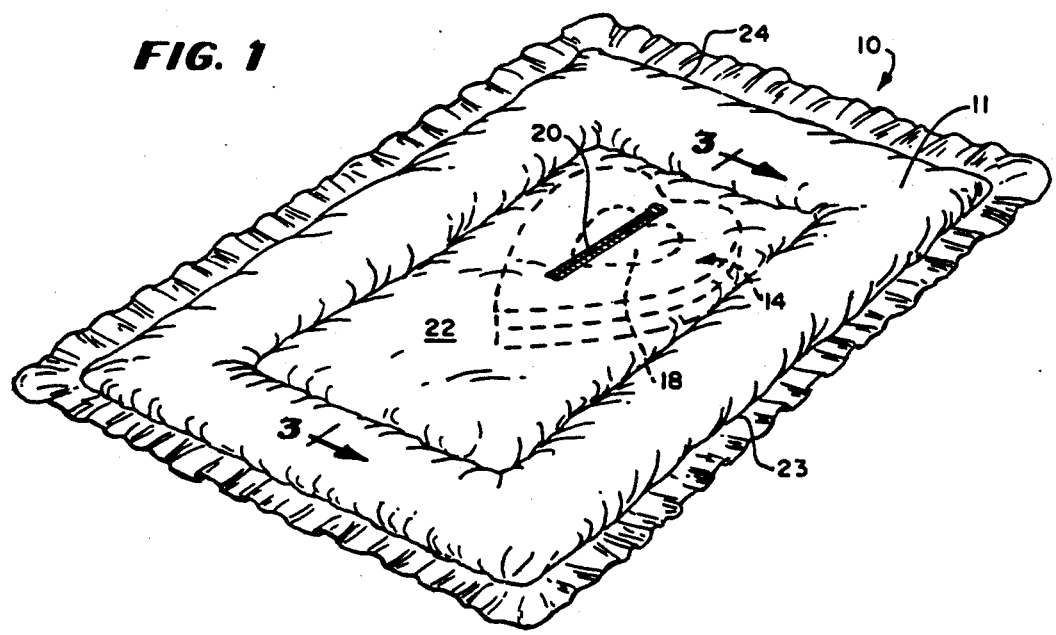
FIG. 1 is a plan view of the baby blanket with heartbeat simulator of the present invention showing placement of the simulator therein in phantom.
Figure 2:
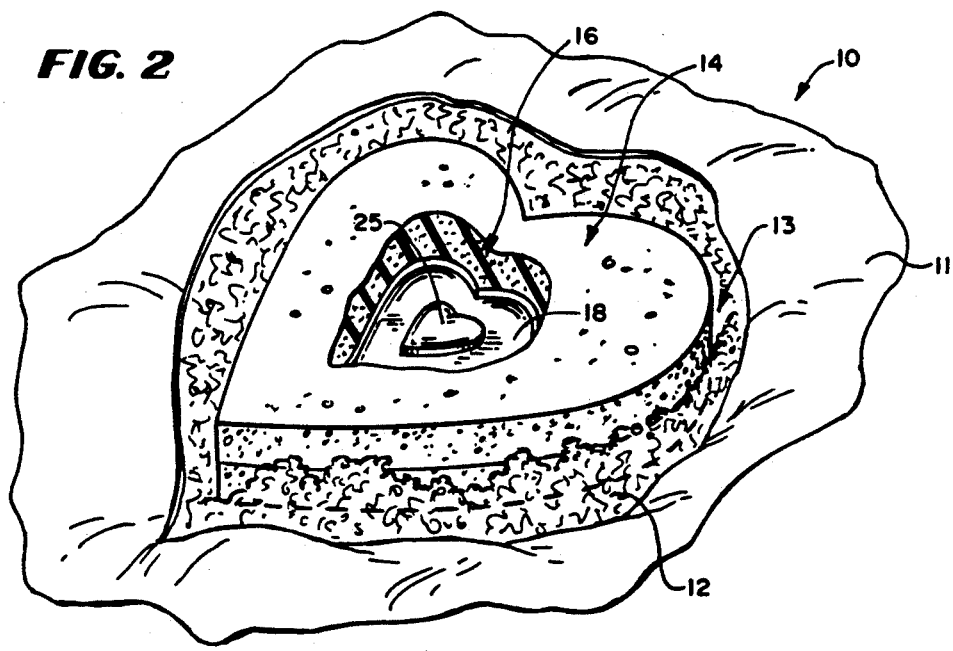
FIG. 2 is an enlarged perspective view with portions broken away to show placement of the simulator within a cushioned cavity for same.
Figure 3:
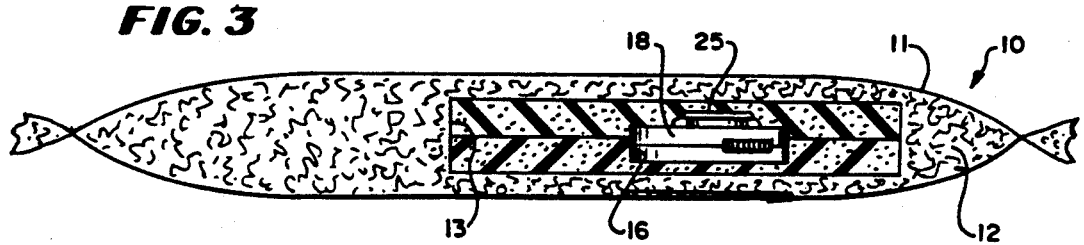
FIG. 3 is a cross sectional view through the blanket and is taken along line 3—3 of FIG. 1.
Figure 4:
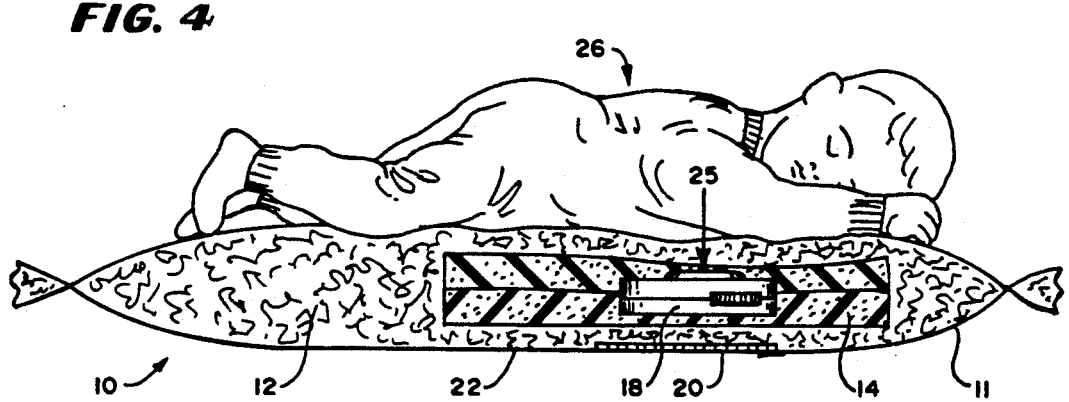
FIG. 4 is a sectional view through the blanket showing the weight of an infant's torso activating the simulator.
Figure 5:
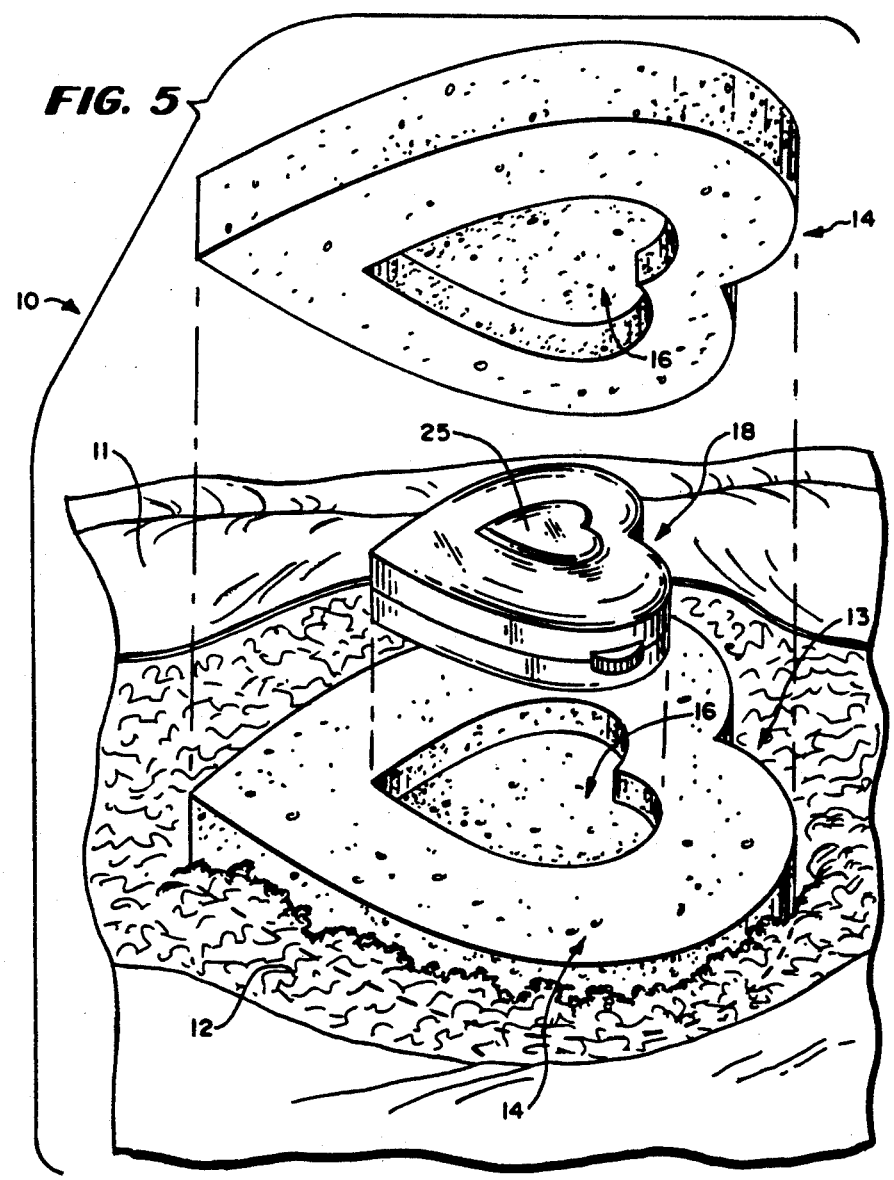
FIG. 5 is an exploded perspective view showing the simulator engaged between pieces of a foam form which create the cushioned cavity therefor.

Referring now to the drawings in greater detail there is illustrated in the Figures an infant blanket made in accordance with the teachings of the present invention and generally identified by reference numeral 10.

The blanket 10 is of the comforter type having an outer shell 11 which is thickly padded with batting material 12 within which a pouch 13 is formed, and includes therein a two piece foam form 14 having a thickness substantially equal to that of the remainder of the blanket 10.

The foam form 14 is heart shaped in the disclosed embodiment and when the pieces are engaged to one another, define a small cavity 16 therein which is also heart shaped in the disclosed embodiment.

Within this small cavity 16 is placed a heartbeat simulator 18 which is pressure activated in the preferred embodiment.

To allow access to the simulator 18, a zipper 20 is provided on one surface 22 of the blanket 10. Such access is necessary for removal of the simulator 18 when it is desired to wash the blanket 10, or for changing a battery (not shown) of the simulator 18.

The blanket 10 includes side edges 23 and end edges 24, with the pouch 13 in the batting 12 centered relative to the side edges 23, and being off center relative to the end edges 24.

In the embodiment of the simulator 18 disclosed, a depressible activation switch 25 is provided thereon. Thus, when an infant 26 is placed upon the blanket 10, the weight of the infant's torso is positioned to overlie the foam form 14 and depress the switch 25, activating the simulator 18.

Conversely, when the weight is removed, the switch 25 disengages, turning the simulator 18 off and conserving the battery.

The two pieces of the foam form 14 are mirror images of one another in the embodiment disclosed, each defining one half of the cavity 16, although this is not to be construed as limiting.

Obviously, the zipper 20 is placed over the area incorporating the foam form 14 and is of a length accommodating removal of the foam form 14. Further, it is understood that the infant 26 is not placed on the surface 22 incorporating the zipper 20, such surface 22 being placed against a surface underlying the blanket 10.

As described above, the blanket 10 of the present invention has a number of advantages, some of which have been described above and others of which are inherent in the invention.

Also modifications can be proposed to the blanket 10 without departing from the teachings herein. Accordingly the scope of the invention is only to be limited as necessitated by the accompanying claims.

I claim:

1. An infant blanket in combination with a removable heartbeat simulator, the improvement comprising said simulator being encased within a foam form and placed within the blanket, said simulator being pressure activated by placement of the weight of an infant's torso in a manner to overlie said simulator.

2. The blanket of claim 1 wherein the blanket comprises a thick comforter comprised a shell of material having batting therein.

3. The blanket of claim 2 wherein a pouch is formed within said batting.

4. The blanket of claim 3 having side edges and end edges and wherein said pouch is centered between said side edges and is offset toward one end edge.

5. The blanket of claim 4 wherein said foam form rests within said pouch.

6. The blanket of claim 5 wherein said foam form comprises two mirror image pieces each defining therein one half of a cavity formed therebetween.

7. The blanket of claim 6 wherein said heartbeat simulator rests within said cavity.

8. The blanket of claim 7 wherein said heartbeat simulator includes a pressure responsive activation switch thereon.

9. The blanket of claim 8 wherein a zipper is provided in one surface thereof to allow for removal of the simulator and foam form from within the blanket.

10. An infant blanket comprising a shell having batting therein, said batting having a pouch formed therein, a foam form defining a cavity therein and being sized and configured to seat within said pouch, and a heartbeat simulator, the cavity in said foam form conforming to the shape of the simulator and with said simulator being encased in said pouch, said pouch being substantially centered within the blanket and the blanket shell including a zipper therein overlying said pouch, said simulator being pressure activated by placement of the weight of an infant's torso in a manner to overlie said simulator.

11. An infant blanket which is in the form of a thick comforter and comprises a heartbeat simulator encased within a foam form having a thickness substantially equal to that of the remainder of the blanket, said thick comforter comprised a shell of material having batting therein, a pouch is formed within said batting, the blanket having side edges and end edges and wherein said pouch is centered between said side edges and is offset toward one end edge, said foam form rests within said pouch, said foam form comprises two mirror image pieces each defining therein one half of a cavity formed therebetween, said heartbeat simulator rests within said cavity, said heartbeat simulator includes a pressure responsive activation switch thereon.

12. The blanket of claim 11 wherein a zipper is provided in one surface thereof to allow for removal of the simulator and foam form from within the blanket.

* * * * *